United States Patent [19]

Haber

[11] Patent Number: 4,892,551
[45] Date of Patent: Jan. 9, 1990

[54] IMPACT DISSIPATING AND LOAD DIVERTING TOTAL HIP ARTHROPLASTY PROSTHESIS

[75] Inventor: Terry M. Haber, Lake Forest, Calif.
[73] Assignee: Habley Medical Technology Corporation, Laguna Hills, Calif.
[21] Appl. No.: 881,638
[22] Filed: Jul. 3, 1986
[51] Int. Cl.⁴ .............................................. A61F 2/32
[52] U.S. Cl. ......................................... 623/23; 623/18
[58] Field of Search ...................................... 623/16-23

[56] References Cited

U.S. PATENT DOCUMENTS

| | | | |
|---|---|---|---|
| 4,224,697 | 9/1980 | Murray et al. | 623/20 |
| 4,262,368 | 4/1981 | Lacey | 623/20 |
| 4,619,659 | 10/1986 | Witzel | 623/23 |

FOREIGN PATENT DOCUMENTS

| | | | |
|---|---|---|---|
| 0046926 | 3/1982 | European Pat. Off. | 623/20 |
| 0066092 | 12/1982 | European Pat. Off. | 623/22 |
| 0099167 | 1/1984 | European Pat. Off. | 623/22 |
| 2247721 | 4/1974 | Fed. Rep. of Germany | 623/23 |
| 2724234 | 12/1977 | Fed. Rep. of Germany | 623/23 |
| 3033227 | 4/1982 | Fed. Rep. of Germany | 623/22 |
| 3336005 | 4/1985 | Fed. Rep. of Germany | 623/18 |
| 1514479 | 6/1978 | United Kingdom | 623/20 |
| 2078523 | 1/1982 | United Kingdom | 623/22 |

Primary Examiner—Richard J. Apley
Assistant Examiner—David J. Isabella
Attorney, Agent, or Firm—Morland C. Fischer

[57] ABSTRACT

A composite total hip arthroplasty prosthesis including a shock-absorbing, elastomeric polymer cushion located between acetabular and subtrocanteric aspects to reduce the impact factor of an intraskeletal load applied through a patient's pelvis to the proximal femur. The arthroplasty prosthesis includes a force transmitting, diverting and dissipating pendulum member which is located at the subtrocanteric aspect and adapted to rotate laterally into contact with the cushion in response to a vertical intraskeletal load. Accordingly, opposing parallel shear forces generated by such intraskeletal loads which are known, in conventional arthroplasty prostheses, to cause scission of tissue ingrowth or shearing fracture of bone cement fixation procedures may be advantageously redirected, dampened and non-linearly decelerated to produce lateral bone formation stimulating loads rather than vertical tissue ingrowth shearing loads between the subtrocanteric aspect of the prosthesis and the proximal femur of the patient.

15 Claims, 2 Drawing Sheets

IMPACT DISSIPATING AND LOAD DIVERTING TOTAL HIP ARTHROPLASTY PROSTHESIS

BACKGROUND OF THE INVENTION

1. Field of the Invention

This invention relates to a composite, impact diverting and force dissipating hip arthroplasty prosthesis characterized by greatly enhanced biocompatibility and wear resistance, wherein potentially damaging shear forces, which are normally transmitted directly to living bone cells through a conventional hard metal arthroplasty prosthesis, are dampened, softened, diverted and non-linearly decelerated before being transmitted to the relatively delicate living bone cells.

2. Prior Art

The conventional hip arthroplasty prosthesis is usually formed from stellite, vitalium, titanium, or the like, acetabular and subtrocanteric elements. Intraskeletal impact forces generated by patient movement are directly transmitted from the pelvis through a conventional arthroplasty prosthesis to a plane of force concentration located at the contact surface between the hard, metallic prosthesis and the relatively soft living bone. Continued impact trauma may induce osteoarthritis or osteomyelitis. Pre-existing osteoporosis may also be aggravated which, in turn, may necessitate explant of the arthroplasty prosthesis and undesirable arthrodesis of the hip joint.

More particularly, with conventional hard metal hip arthroplasty prosthesis, equal and opposite forces are generated by the arthroplasty prostheses in response to applied, vertical intraskeletal loads. Such opposing forces produce parallel shear planes which may undesirably exceed the fatigue strength of bone cement fixation procedures or cause scission of stabilizing tissue ingrowth between the patient's bone and the conventional hip arthroplasty prostheses. The failure of the conventional hip arthroplasty prostheses to effectively divert, dissipate or absorb intraskeletal loads reduces the biocompatibility, longevity and patient comfort of such arthroplasty prostheses.

SUMMARY OF THE INVENTION

Briefly, and in general terms, an improved impact diverting and dissipating hip arthroplasty prosthesis is disclosed which is uniquely adapted to redirect, reduce and/or absorb potential tissue destroying shear impact forces imparted therethrough. A shock-absorbing cushion or suspension is located through the hip arthroplasty prosthesis and between acetabular and subtrocanteric aspects thereof to reduce the impact of an intraskeletal load applied through the patient's pelvis to the proximal femur. The present hip arthroplasty prosthesis includes a force transmitting, diverting and dissipating pendulum member which is located at the subtrocanteric aspect and adapted to rotate laterally into engagement with the cushion or suspension in response to a vertical intraskeletal load. The shock-absorbing cushion or suspension is thereby non-linearly compressed so as to dampen or absorb such intraskeletal load. Accordingly, rotation of the pendulum acts to mechanically transform vertical shocks into dampened, eccentric and lateral compression loads to be automatically, gently, and non-linearly decelerated and dissipated. As an advantageous result of the foregoing, opposing parallel impact shear forces, known in conventional arthroplasty prostheses to sever tissue growth or fracture bone cement, may be redirected to non-shearing levels before transmission to the proximal femur. In this manner, the formation and growth of bone tissue ingrowth is stimulated rather than resorbed.

DESCRIPTION OF THE PREFERRED EMBODIMENT

Figures 1, 2:
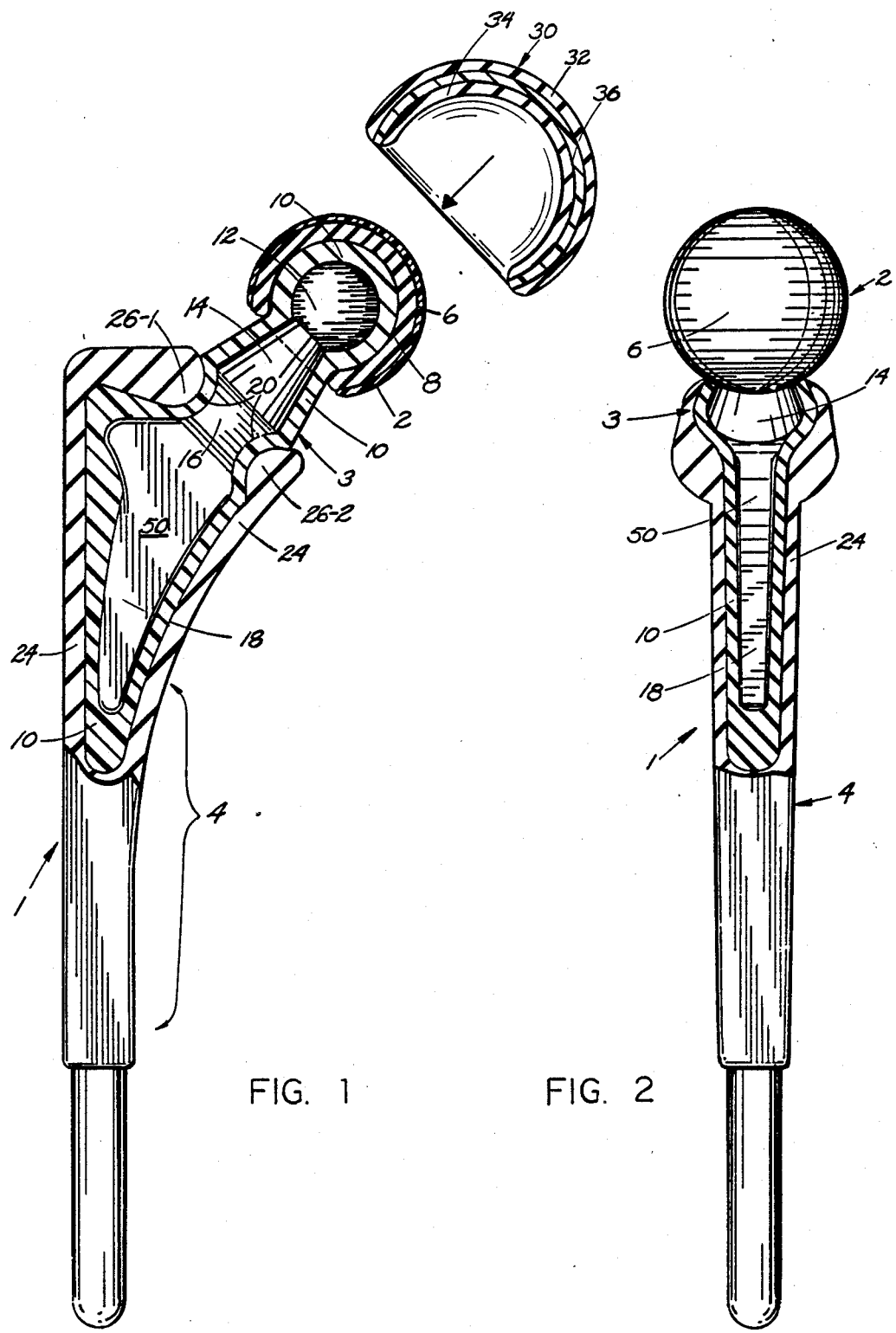
FIG. 1 shows a side view, in partial cross-section, of the impact dissipating hip arthroplasty prosthesis which forms the present invention.
FIG. 2 is a front view of the hip arthroplasty prosthesis of FIG. 1.

The hip arthroplasty prosthesis 1 which forms the present invention is initially described while referring concurrently to FIGS. 1 and 2 of the drawings. The hip arthroplasty prothesis 1 has a one-piece investment casting 50 comprising integrally connected portions of an intertrocanteric aspect a shank 3 and a subtrocanteric aspect 4. Investment casting 50 is preferably fabricated from a suitable wear-resistant, biocompatible, and structurally hard material such as titanium, or the like. The intertrocanteric aspect 2 of hip arthroplasty prosthesis 1 includes an outer concave bearing surface 6 formed from a suitable bearing material, such as polyethylene, or the like. Located below bearing surface 6 is a concave, metallic spacer 8. Spacer 8 extends over a shock absorbing cushion or suspension 10 that is formed from a suitable high durometer, high tear strength, elastomeric polymer or metallic spring means, such as polyurethane, or the like. Cushion or suspension 10 extends over and around a spherical bearing 12 to absorb and minimize shock that may be transmitted through the intertrocanteric aspect 2 to a patient's proximal femur when spherical bearing 12 is subjected to an intraskeletal load.

The shank 3 of hip arthroplasty prosthesis 1 extends between the intertrocanteric and subtrocanteric aspects 2 and 4 and includes a generally conically-shaped neck 14. Cushion or suspension 10, which covers bearing 12, also extends around the neck 14. Interconnecting the shank 3 and subtrocanteric aspect 4 of hip arthroplasty prosthesis 1 is a fulcrum locator 16. More particularly, fulcrum locator 16 comprises a coextensive region of reduced cross-sectional area extending between the neck 14 of shank 3 and a pendulum 18 of subtrocanteric aspect 4. The periphery of the reduced area of fulcrum locator 16 forms an arcuate surface by which to receive a fulcrum 20 and permit pendulum 18 to rotate, an important advantage of this invention which will be described in greater detail when referring hereinafter to FIGS. 3 and 4.

The aforementioned cushion or suspension 10, which covers spherical bearing 12 and neck 14, extends continuously along the subtrocanteric aspect 4 to also surround fulcrum locator 16 to redirect and dampen the transmission of vertical loads to the patient's proximal femur when pendulum 18 is caused to rotate at fulcrum locator 16. Surrounding the cushion or suspension 10 of subtrocanteric aspect 4 is a biocompatible, wear-resistant investment cast outer shell 24 which is formed from a suitable metal material, such as titanium, or the like. Cushion or suspension 10 provides an elastomeric or spring-like region through which pendulum 18 may rotate, in a manner to be described, such that the known spring constant of cushion or suspension 10 will be compressed against the outer shell 24. Shell 24 terminates at an upper concave lip comprising dorsal and ventral aspects 26-1 and 26-2 which form a fulcrum 20 that is dimensioned to be received at the arcuate pivot surface around fulcrum locator 16. However, and as is best shown in FIG. 1, a portion of the cushion or suspension 10 is disposed between the fulcrum locator 16 and fulcrum 20 to avoid metal-to-metal surface contact and thereby minimize friction and wear whenever pendulum 18 rotates around the pivotal interface formed between fulcrum locator 16 and the dorsal and ventral aspects 26-1 and 26-2 of fulcrum 20.

As is also best shown in FIG. 1, a concave acetabular aspect 30 is provided to receive therewithin the intertrocanteric aspect 2 of hip arthroplasty prosthesis 1. More particularly, acetabular aspect 30 includes a metallic outer bearing surface 32 and a metallic inner socket surface 34. With hip arthroplasty prosthesis 1 suitably positioned, outer bearing surface 32 will be fixedly retained in the patient's pelvis and inner socket surface 34 will receive the outer bearing surface 6 of intertrocanteric aspect 2 (best shown in FIGS. 3 and 4) to support a torsional rotation of spherical bearing 12, when the patient's pelvis and proximal femur are rotated axially relative to one another. Disposed between the outer bearing and inner socket surfaces 32 and 34 of acetabular aspect 30 is a cushion or suspension 36 which avoids metal-to-metal contact between surfaces 32 and 34.

Figures 3, 4:
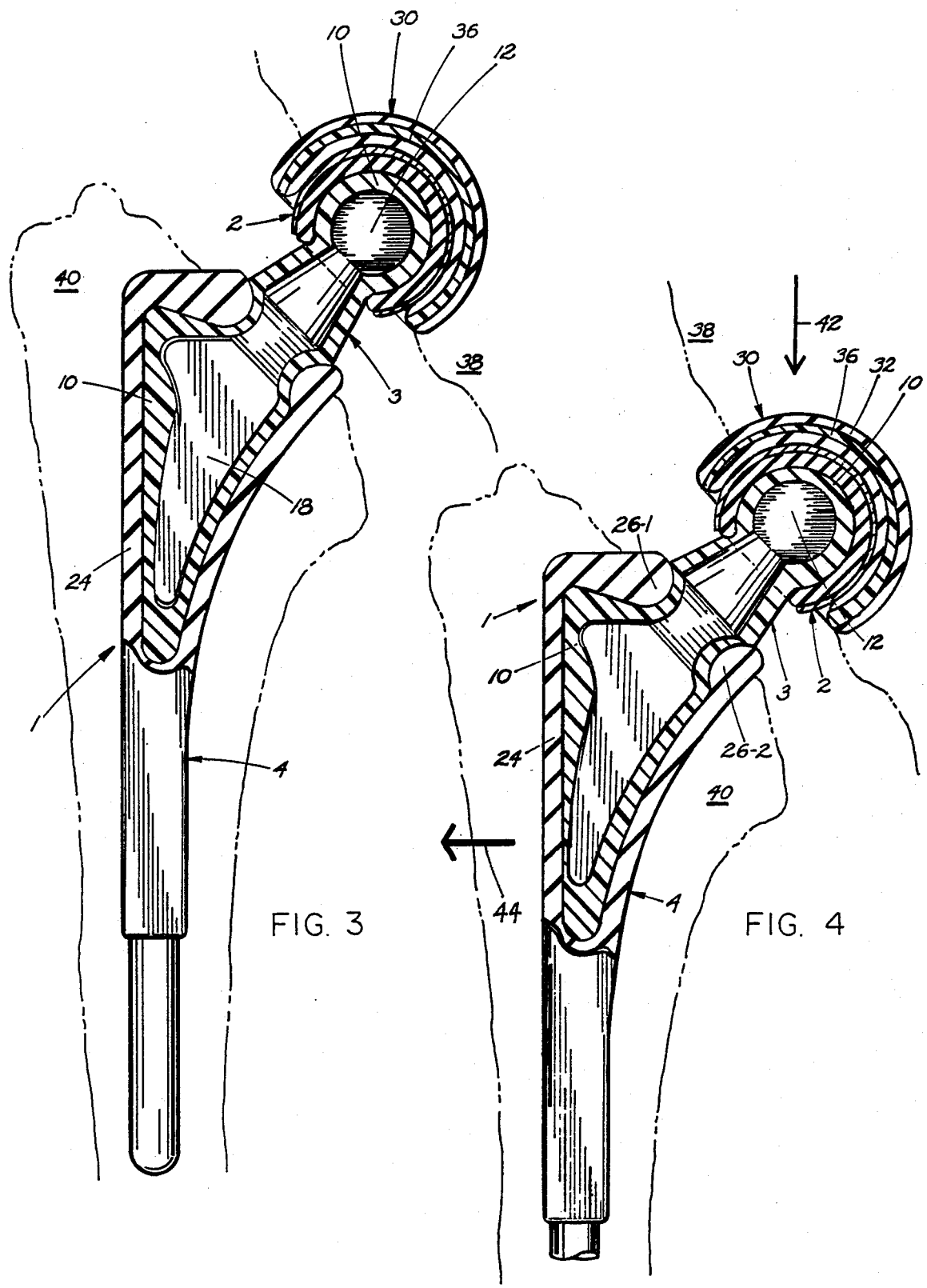
FIG. 3 shows the hip arthroplasty prosthesis being at rest and extending between the patient's pelvis and proximal femur.
FIG. 4 shows the hip arthroplasty prosthesis of FIG. 3 under an intraskeletal load.

The operation of the presently described hip arthroplasty prosthesis to redirect, reduce and/or partially absorb the application of potential tissue destroying shear forces to the proximal femur is now disclosed when referring to FIGS. 3 and 4 of the drawings. FIG. 3 shows the hip arthroplasty prosthesis 1 at rest (i.e. with no intraskeletal loads being applied to acetabular aspect 30). In the assembled relationship of FIGS. 3 and 4, the subtrocanteric aspect 4 is surgically implanted within the patient's proximal femur 40, and the acetabular aspect 30 is surgically affixed into the patient's pelvis 38. As previously disclosed, the intertrocanteric aspect 2 is received within acetabular aspect 30. Accordingly, the shank 3 extends between the patient's pelvis 38 and proximal femur 40, such that spherical bearing 12 and pendulum 18 are free to rotate, as will now be described in detail.

In FIG. 4, an intraskeletal load, which is generated by patient movement, is applied to acetabular aspect 30 in a generally vertical direction indicated by arrow 42. Unlike conventional hip arthroplasty prostheses, the presence of load-absorbing cushion or suspensions 10 and 36 between acetabular and subtrocanteric aspects 4 and 30 of hip arthroplasty prosthesis 1 advantageously acts as a buffer to absorb the shock and reduce the impact of any such intraskeletal load applied to the patient's proximal femur 40. Moreover, and as earlier described, the patient's bone, in which a conventional hip arthroplasty prosthesis is implanted, would normally generate an equal and oppositely directed force to oppose the vertical intraskeletal load 42. Such opposing forces would often produce parallel shear planes which may undesirably fracture the bone cement of cemented prosthesis procedures or shear away any stabilizing tissue ingrowth between the patient's bone and the hip arthroplasty prosthesis.

However, and by virtue of the present invention, the parallel shear forces, common to conventional hip arthroplasty prostheses, are advantageously dampened, decelerated and diverted into laterally oriented non-shearing vectors. More particularly, in response to vertical intraskeletal load 42, the hip arthroplasty prosthesis 1 generates a lateral force in a direction indicated by vector 44, which direction is transverse to the direction of load 42. That is, the application of a vertical intraskeletal load 42 causes the pendulum 18 at subtrocanteric aspect 4 to rotate around fulcrum 20 at the interface of dorsal and ventral aspects 26-1 and 26-2 with the fulcrum locator 16. During such rotation of pendulum 18 (in the direction of vector 44), the cushion or suspension 10 is compressed against outer shell 24. In this manner, and with pendulum 18 rotating within the subtrocanteric aspect 4, the intraskeletal load 42 may be redirected, absorbed and dampened within hip arthroplasty prosthesis 1 prior to its transmission to proximal femur 40. Thus, the fulcrum locator 16 acts to mechanically redirect vertical, tissue shearing shocks into dampened, eccentric and lateral compression loads to be automatically, gently, and non-linearly decelerated and finally dissipated by the rotation of pendulum 18 through the load absorbing cushion or suspension 10. What is more, the formation of bone tissue ingrowth is stimulated, rather than resorbed. Of course, when the intraskeletal load 42 is removed, the elastomeric or spring-like nature of cushion or suspension 10 will urge the pendulum 18 to rotate (in a direction opposite that indicated by vector 44) back to the at rest position of FIG. 3.

By virtue of the present invention, a unique hip arthroplasty prosthesis is available which effectively redirects, reduces and absorbs intraskeletal loads applied thereto. Accordingly, bone tissue ingrowth around the hip arthroplasty prosthesis is stimulated and destructive deformation of the patient's bone is minimized. What is more, the improved hip arthroplasty prosthesis is characterized by enhanced biocompatibility, shorter surgical recovery time and greater device longevity which greatly reduces the risk of osteoarthritis or osteomyelitis and the possibility of prosthesis explant and subsequent arthrodesis of the hip joint.

It will be apparent that while a preferred embodiment of the invention has been shown and described, various modifications and changes may be made without departing from the true spirit and scope of the invention. For example, although the present invention has been described with respect to a hip arthroplasty prosthesis, it is to be specifically recognized that the teachings of this invention are applicable to other suitable prosthetic joints. By way of further example, although an elastomeric cushioning polymer has been described with respect to a hip arthroplasty prosthesis, it is to be specifically recognized that the teachings of this invention may also employ a more conventional metallic, spherical or leaf-type cushioning or springing means.

Having thus set forth a preferred embodiment of this invention, what is claimed is:

1. An impact dissipating hip arthroplasty prosthesis for interconnecting first and second bones of a patient, said prosthesis having a head portion attached at a first of the patient's bones, and a body portion attached at the second of the bones and having an inwardly extending surface that forms a fulcrum, said prosthesis including a one piece impact dissipating member extending from said head portion to be received within said body portion and supported at said fulcrum, said impact dissipating member being rotatable in a first direction within said body portion and around said fulcrum in response to an intraskeletal load applied in a second, transverse direction through the patient's first bone so as to redirect and decelerate the load and reduce the shock effect of such load on the patient's second bone.

2. The prosthesis recited in claim 1, including shock absorbing means extending around said impact dissipating member to absorb the intraskeletal load when said impact dissipating member is rotated.

3. The prosthesis recited in claim 1, including socket means located at the patient's first bone for receiving said head portion therewithin and positioning said head portion with respect to said bone, said socket means having shock absorbing means for absorbing the intraskeletal load applied through the patient's first bone.

4. The prosthesis recited in claim 1, wherein said impact dissipating member includes a region of relatively narrow cross-section, said region being received by said fulcrum for permitting said impact dissipating member to rotate.

5. The prosthesis recited in claim 4, wherein said body portion includes an outer shell for surrounding an end of said impact dissipating member, said outer shell having a lip extending therearound to be received at the region of relatively narrow cross-section of said impact dissipating member and thereby forming the fulcrum around which said impact dissipating member rotates.

6. The prosthesis recited in claim 1, wherein said head portion includes a rotatable spherical bearing and a bearing surface surrounding said spherical bearing to support rotational movement of said bearing and reduce wear of said bearing when the patient's first and second bones are moved relative to one another, and shock absorbing cushion means extending between said spherical bearing and said bearing surface to absorb the intraskeletal load applied through the patient's first bone.

7. The prosthesis recited in claim 1, wherein said body portion includes an outer shell for surrounding an end of said impact dissipating member, and shock absorbing means extending between said outer shell and said end of said impact dissipating member to absorb the intraskeletal load when said impact dissipating member rotates, such that said cushion means is compressed between said end and said outer shell.

8. An impact diverting and dissipating hip arthroplasty prosthesis extending between first and second bones of a patient's body and comprising:
   an outer shell;
   a one piece impact transmitting, redirecting and dissipating member received within said outer shell and extending continuously between said first and second bones;
   pivot surface means located within said outer shell to support said impact transmitting and dissipating member for rotational movement therearound; and
   shock absorbing cushion means located between said outer shell and said impact transmitting and directing dissipating member;
   an intraskeletal load transmitted in a first direction through a first of the patient's bones causing said impact transmitting, redirecting and dissipating member to rotate in a second, transverse direction within said outer shell and around said pivot surface means, such that said cushion means is compressed against said outer shell to redirect, absorb and decelerate the intraskeletal load and thereby reduce the shock effect of such load on the second of the patient's bones.

9. The prosthesis recited in claim 8, wherein said impact transmitting, redirecting and dissipating member includes a region of relatively narrow cross-section, said region being supported at said pivot surface means for permitting said member to rotate.

10. The prosthesis recited in claim 9, wherein said outer shell has a lip extending therearound to be received at the region of relatively narrow cross-section of said impact transmitting, redirecting and dissipating member for forming the pivot surface means around which said member rotates.

11. The prosthesis recited in claim 10, wherein said cushion means extends between the lip of said outer shell and the relatively narrow cross-section region of said impact transmitting, redirecting and dissipating member for reducing friction at said pivot surface means when said member rotates therearound.

12. The prosthesis recited in claim 8, further comprising a rotatable spherical bearing to be located at the patient's first bone, a bearing surface surrounding said spherical bearing to support rotational movement of said bearing when the patient's first and second bones are moved relative to one another, and said cushion means extending between said spherical bearing and said bearing surface to absorb some of the intraskeletal load transmitted through said first bone.

13. The prosthesis recited in claim 12, further comprising socket means attached to the patient's first bone for receiving said bearing surface therewithin and thereby locating said spherical bearing at said first bone, said socket means having shock absorbing cushion means for absorbing some of the intraskeletal load transmitted through said first bone.

14. An impact dissipating hip arthroplasty prosthesis extending between first and second bones of a patient and comprising:
   a one piece impact dissipating and force redirecting member extending continuously between said first and second bones;
   an outer shell having a hollow interior to surround at least some of said impact dissipating and force redirecting member, said outer shell including fulcrum means located at the interior thereof upon which to support said impact dissipating and force redirecting member for pivotal movement therearound; and
   shock absorbing means located between the interior of said outer shell and said impact dissipating and force redirecting member;
   an intraskeletal load transmitted through a first of the patient's bones causing said impact dissipating and force redirecting member of pivot within the hollow interior of said outer shell and around said fulcrum means in a direction transverse to the direction of said load, such that said cushion means is compressed by said member against said outer shell to redirect, absorb and decelerate the intraskeletal load and thereby reduce the shock of said load on the second of the patient's bones.

15. The prosthesis recited in claim 14, wherein said impact dissipating and force redirecting member includes a recessed fulcrum locating region in which to receive the fulcrum means of said outer shell, so that said member may pivot around said fulcrum means.

* * * * *